US00PP26850P3

(12) United States Plant Patent
Schoone

(10) Patent No.: US PP26,850 P3
(45) Date of Patent: Jun. 21, 2016

(54) ***PHALAENOPSIS* ORCHID PLANT NAMED 'LATE FROST'**

(50) Latin Name: *Phalaenopsis hybrida*
Varietal Denomination: Late Frost

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 138 days.

(21) Appl. No.: 13/999,402

(22) Filed: Feb. 24, 2014

(65) Prior Publication Data

US 2014/0317805 P1 Oct. 23, 2014

(30) Foreign Application Priority Data

Apr. 25, 2013 (NL) ..... PBR OPS1024

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — June Hwu
(74) *Attorney, Agent, or Firm* — Foley & Lardner LLP; Sunit Talapatra

(57) ABSTRACT

A new and distinct *Phalaenopsis* plant named 'Late Frost' particularly characterized by flowers which are white with some yellow in the labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Late Frost'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Late Frost'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Late Frost' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Late Frost' originated from a cross made by the inventor in 2000 in Strengweg, Heemskerk, The Netherlands. The female or seed parent is the *Phalaenopsis* cultivar designated 'Hawaiian Pearl', unpatented. The male or pollen parent is an unnamed, unpatented cultivar of *Phalaenopsis amabilis*. The new *Phalaenopsis* 'Late Frost' was discovered and selected by the inventor as a single flowering plant within the progeny of the stated cross in a controlled environment in 2008 in Strengweg, Heemskerk, The Netherlands.

Asexual reproduction of the new *Phalaenopsis* cultivar by tissue culture (mericloning) was first performed in November, 2008 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Late Frost', which in combination distinguish this *Phalaenopsis* as a new and distinct cultivar:

1. flowers which are white with some yellow in the labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Late Frost', the female parent 'Hawaiian Pearl' has white flowers and they are about 12 cm in size, the male parent (unnamed, unpatented cultivar of *Phalaenopsis amabilis*) has white colored flowers and they are about 7 cm in size, whereas the flowers of 'Late Frost' are white and are about 11 cm in size.

Presently, the commercial cultivars to which 'Late Frost' can be meaningfully compared are 'Lively' (U.S. Plant patent application Ser. No. 13/999,401) and 'Honeymoon' (U.S. Plant Pat. No. 26,292). The size of the petals and sepals differs and the size of the cirrhi differs between these three cultivars. Also the amount of yellow on the cirrhi differs. The midlobe of 'Lively' has a red/purple edge on the upper side and 'Honeymoon' has a purple haze on the midlobe, whereas on the midlobe of 'Late Frost' there is orange/red and purple/violet. The amount of yellow on the midlobe also differs.

BRIEF DESCRIPTION OF THE PHOTOGRAPHS

The accompanying photographs illustrate the overall appearance of the new *Phalaenopsis* 'Late Frost' showing the colors as true as is reasonably possible with colored reproductions of this type. Colors in the photographs may differ slightly from the color values cited in the detailed botanical description, which accurately describe the color of 'Late Frost'.

DETAILED BOTANICAL DESCRIPTION

Figure 1:
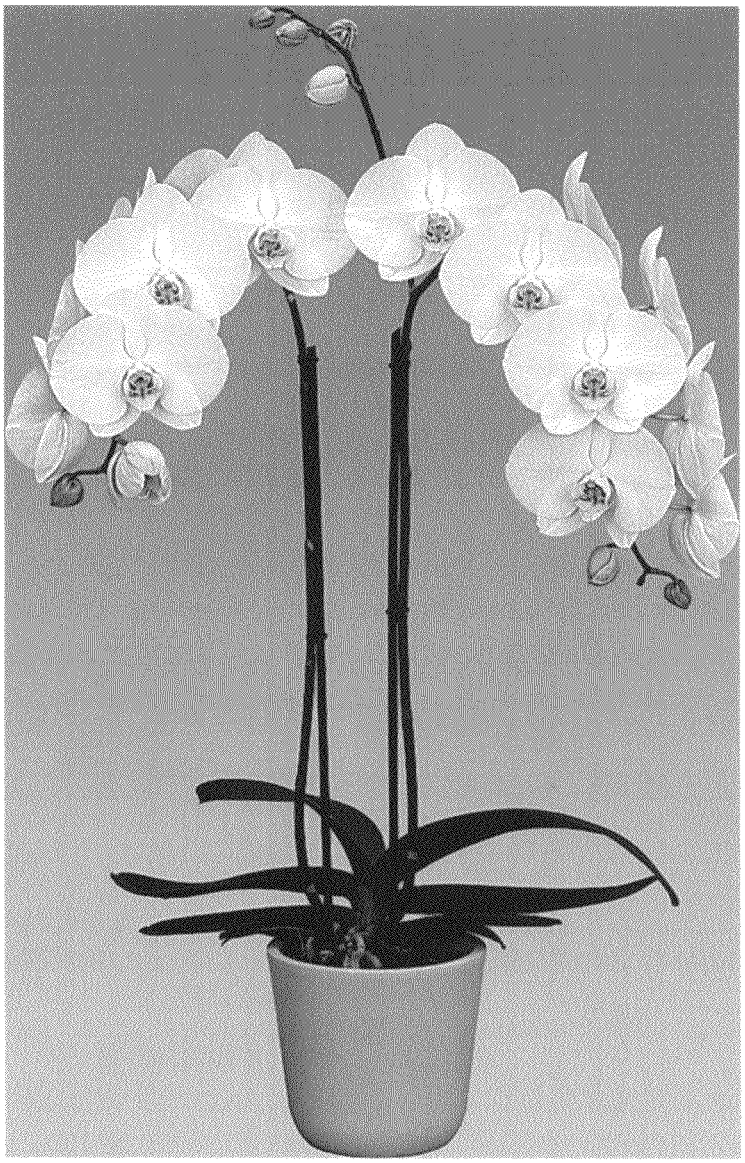
FIG. 1 shows a side view perspective of a typical flowering plant of 'Late Frost' in a 12 cm pot, at 16 months of age.

The new *Phalaenopsis* cultivar 'Late Frost' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Late Frost' as grown in a greenhouse in Strengweg, Heemskerk, The Netherlands, under conditions which closely approximate those generally used in commercial practice. Initially, the ideal temperature to grow plants of 'Late Frost' is 27° C. during the day and at night. Then, during the flowering phase of 'Late Frost', the ideal growing temperature is 20-22° C. during the day and 18° C. at night. Light levels for growing 'Late Frost' are a minimum of 5,000 lux and a maximum of 10,000 lux. A balanced fertilizer with level of 200 ppm N, 87 ppm P, 168 ppm K is applied. Duration of growth of 'Late Frost' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Late Frost' plants described is 12 months after potting.

Classification:

*Botanical.*—*Phalaenopsis hybrida.*

Parentage:

*Female or seed parent.*—*Phalaenopsis* cultivar designated 'Hawaiian Pearl', unpatented.

*Male or pollen parent.*—Unnamed, unpatented cultivar of *Phalaenopsis amabilis.*

Propagation:

*Type.*—Tissue culture (mericloning).

*Rooting habit and description.*—Fleshy; approximately 4 mm-7 mm wide and greyed/green in color (RHS 194A and RHS N189D); freely branching. It takes 12 weeks for plants growing in tissue culture to initiate roots.

Plant:

*Size at maturity.*—Height (from bottom of pot to highest flower): about 60 to 70 cm. Spread: about 40 to 70 cm.

*Growth habit.*—Standard; green leaves (RHS 137B) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 racemes with flowers appear.

Foliage:

*Quantity per plant.*—About 6 to 10 leaves are produced before flowering.

*Arrangement and attachment.*—Alternate, clasping.

*Overall shape of leaf.*—Oval, the tip is blunt and asymmetric.

*Texture* (*upper & underside*).—Smooth and leathery.

*Pubescence.*—None.

*Mature leaf length.*—About 15 to 25 cm.

*Mature leaf width.*—About 7 to 10 cm.

*Mature leaf thickness.*—About 2 mm.

*Mature leaf color.*—Upper side: green (RHS 137B). Under side: combination of yellow/green (RHS 144A) and green (RHS 137D).

*Leaf base.*—Acute.

*Margin.*—Entire.

*Venation.*—Pattern: parallel. Color of midvein: Upper side: green (RHS 137B). Under side: yellow/green (RHS 144A).

Inflorescence description:

*Appearance.*—Upright to slightly pendant, racemose inflorescence with bilaterally symmetrical flowers that open in succession beginning with the lowermost flower.

*Raceme.*—Quantity per plant: about 1 to 2. Number of flowers per raceme: about 10 to 20. Length: about 65 to 70 cm.

*Peduncle.*—Diameter: about 7 mm. Strength: strong. Aspect: upright. Texture: glabrous and smooth. Color: green (RHS N137A) with RHS 137D.

*Buds.*—Height (from base to tip): about 25 mm. Diameter (at midpoint): about 20 mm. Shape: oval with a bump on the side. Color: yellow/green (RHS 145A and RHS 145B) with a little purple/violet (RHS N81B).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
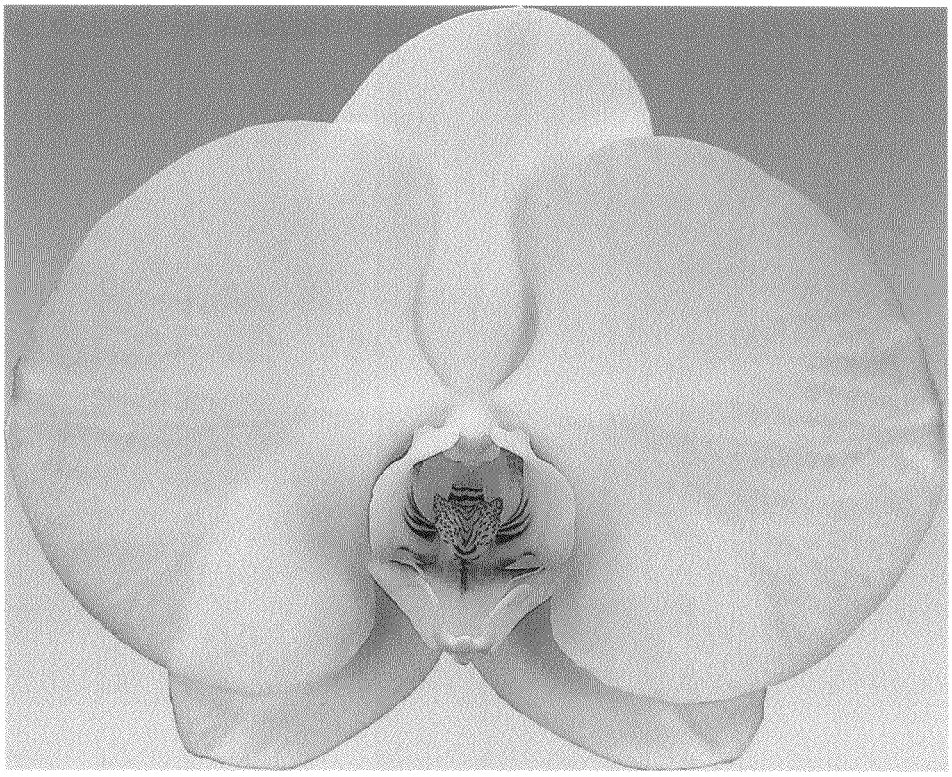
FIG. 2 shows a close-up view of a typical flower of 'Late Frost'.
Figure 3:
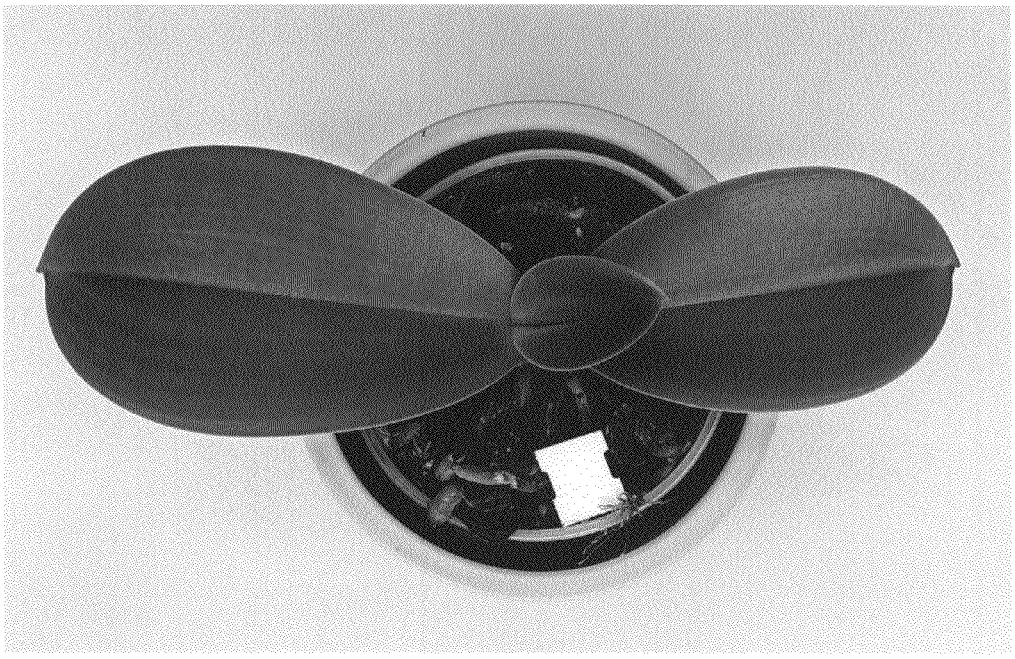
FIG. 3 shows a close-up view of the typical leaves of 'Late Frost'.

*Flower*.—Rate of opening: Flowers fully opened about 2 to 3 days after petal and sepal separation. Orientation at opening: slanted upward and outward. Shape: Typical shape of *Phalaenopsis*; see FIG. 2. Size (of single bloom): Height: about 10 cm. Diameter: about 11 cm. Quantity and arrangement: three petals and three sepals that are trimerous and arranged in 2 overlapping whorls. Inner whorl of three petals is comprised of 2 lateral petals and a labellum. Petals are more pronounced than sepals.

*Petals*.—2 lateral petals: Overall shape: broadly ovate and weakly cupped. Apex: oval. Margin: entire and weakly undulate. Base: broadly ovate. Length: about 65 mm. Width: about 55 mm. Texture: Upper surface: smooth and satiny. Under surface: smooth and satiny. Color (when fully opened): upper and under surface: white (RHS NN155C). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Apex: oval. Length midlobe: about 25 mm. Width midlobe (not flattened): about 30 mm. Length lateral lobe: about 18 mm. Width lateral lobe (not flattened): about 20 mm. Depth of tube created by lateral lobes of labellum: about 20 mm. Texture: Upper and under surface: smooth and satiny. Color (when fully opened): Mid lobe, upper surface: main color is white (RHS NN155C). From base upper edge is orange/red (RHS N34A). Also from base at the mid vein a small orange/red line (RHS N34A). At the base, on both sides of the mid vein a little purple/violet (RHS N81D). Both corners and in the center yellow (RHS 5C). Under surface: main color is white (RHS NN155C). At the base in the center edge of purple/violet (RHS N81D). Upper edges at the base are orange/red (RHS N34A). Corners are yellow (RHS 5C). Lateral lobes, upper surface: main color is white (RHS NN155C). Lower edge is yellow (RHS 6B). From base some red/purple stripes (RHS 71A) and some greyed/purple stripes (RHS 185D). Under surface: main color is white (RHS NN155C). Lower edge is yellow (RHS 6B) which runs into RHS 6D. At the base a little bit purple/violet (RHS N81B). Cirrhi: about 32 mm and curly. color: first white (RHS NN155C), then yellow (RHS 6A). Pestle (Callosities): Length: about 6 mm. Width (not flattened): about 8 mm. Pubescence: None. Color: white (RHS NN155A). Front and top are yellow (RHS 9A) with red/purple spots (RHS 59B).

*Sepals*.—Arrangement: Outer whorl comprises 3 sepals, one dorsal and two lateral sepals. Overall shape: elliptical and weakly cupped. Margin: entire and weakly undulate. Length: about 53 mm. Width: about 37 mm. Apex: oval; lateral sepals little pointy. Texture: Upper and under surface: smooth and satiny. Color (when fully opened): Dorsal, upper surface: white (RHS NN155C). Under surface: white (RHS 155C) with in the top a purple/violet haze (RHS N81C). Lateral, upper surface: white (RHS NN155C). At the base some purple/violet spots (RHS N81C). Under surface: white (RHS NN155C) with a purple/violet haze (RHS N81C) and a yellow/green haze (RHS 145C).

*Pedicel*.—Length: about 40 mm. Diameter: about 4 mm. Texture: glabrous and smooth. Color: white (RHS NN155B) with a purple haze (RHS N78BN) which runs into yellow/green (RHS 145B) and then into RHS 146C.

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed or fruit.

*Column*.—Length: about 8 mm. Diameter: about 6 mm. Color: white (RHS NN155C).

*Pollinia*.—Quantity: two. Diameter: about 2 mm. Color: orange (RHS 24A).

*Ovary*.—Length: about 4 mm. Diameter: about 6 mm. Color: white (RHS NN155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Late Frost', as illustrated and described herein.

* * * * *